United States Patent
Fukumoto

(10) Patent No.: US 11,186,605 B2
(45) Date of Patent: Nov. 30, 2021

(54) CRYSTAL OF CYTIDINE DIPHOSPHATE CHOLINE AND PRODUCTION METHOD THEREOF

(71) Applicant: KYOWA HAKKO BIO CO., LTD., Tokyo (JP)

(72) Inventor: Kazunari Fukumoto, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 16/339,301

(22) PCT Filed: Oct. 6, 2017

(86) PCT No.: PCT/JP2017/036463
§ 371 (c)(1),
(2) Date: Apr. 3, 2019

(87) PCT Pub. No.: WO2018/066690
PCT Pub. Date: Apr. 12, 2018

(65) Prior Publication Data
US 2019/0225642 A1 Jul. 25, 2019

(30) Foreign Application Priority Data
Oct. 6, 2016 (JP) .............................. JP2016-197695

(51) Int. Cl.
*C07H 19/10* (2006.01)
*C07H 1/06* (2006.01)

(52) U.S. Cl.
CPC .............. *C07H 19/10* (2013.01); *C07H 1/06* (2013.01); *C07B 2200/13* (2013.01)

(58) Field of Classification Search
CPC ........... C07H 19/06; C07H 19/10; C07H 1/06
See application file for complete search history.

(56) References Cited

U.S. PATENT DOCUMENTS

| | | | | |
|---|---|---|---|---|
| 3,687,932 A | * | 8/1972 | Nakamachi | ............ C07H 19/10 536/26.23 |
| 2009/0286284 A1 | | 11/2009 | Murata et al. | |
| 2010/0099847 A1 | | 4/2010 | Shimose et al. | |
| 2010/0222590 A1 | | 9/2010 | Aoki et al. | |
| 2010/0256212 A1 | | 10/2010 | Leksic et al. | |

FOREIGN PATENT DOCUMENTS

| | | |
|---|---|---|
| CN | 101538300 A | 9/2009 |
| CN | 103319504 A | 9/2013 |
| JP | S46-037749 B | 11/1971 |
| JP | S51-032630 B | 9/1976 |
| JP | S51-108076 A | 9/1976 |
| RU | 2408597 C2 | 1/2010 |

OTHER PUBLICATIONS

Japanese Patent Office, International Search Report in International Patent Application No. PCT/JP2017/036463 (dated Dec. 5, 2017).
Japanese Patent Office, Written Opinion of the International Searching Authority in International Patent Application No. PCT/JP2017/036463 (dated Dec. 5, 2017).
Japanese Patent Office, International Preliminary Report on Patentability of the International Searching Authority in International Patent Application No. PCT/JP2017/036463 (dated Apr. 9, 2019).
Kikugawa et al., "Synthesis of a Nucleotide Coenzyme, CDP-Choline," *Chem. Pharm. Bull.*, 19(5): 1011-1016 (1971).
Kikugawa et al., "Studies on the Vilsmeier-Haack Reaction. III. Synthesis of Cytidine Diphosphate Choline," *Chem. Pharm. Bull.*, 19(12): 2466-2471 (1971).
European Patent Office, Extended European Search Report in European Patent Application No. 17858526.1 (dated May 14, 2020).
Sigma-Aldrich, Specification Sheet for Ethanol, ACS Reagent Grade ~96% (2020) [downloaded from https://www.sigmaaldrich.com/catalog/DataSheetPage.do?brandKey=SIGALD&symbol=02870].
Australian Patent Office, Examination Report for Australian Patent Application No. 2017341136 (dated Dec. 18, 2020).
Nakamachi et al., "Cytidine 5'-Diphosphate Choline Monohydrate," *J. Takeda Res. Lab.*, 34(3): 358-368 (1975).
Caira, "Crystalline Polymorphism of Organic Compounds," *Topics in Current Chemistry*, 198: 163-208 (1998).
Knuniants (ed.), "Crystals" in the *Encyclopedia of Chemistry*, 2: 536-540 (1998).
Wenz et al., "More Space for Regenerable Bone Tissues," *New in Dentistry*, 1: 60-64 (2004).
Russian Patent Office, Official Action in Russian Patent Application No. 2019112721 (dated Jan. 26, 2021).

* cited by examiner

*Primary Examiner* — Pancham Bakshi
(74) *Attorney, Agent, or Firm* — Leydig, Voit & Mayer, Ltd.

(57) ABSTRACT

An object of the present invention is to provide a crystal of cytidine diphosphate choline which contains no methanol and has improved powder properties, and a production method thereof. According to the present invention, the crystal of cytidine diphosphate choline which contains no methanol and has improved powder properties can be obtained by precipitating the crystal of cytidine diphosphate choline in an aqueous solution in which cytidine diphosphate choline is dissolved, collecting the precipitated crystal of cytidine diphosphate choline, and washing the collected crystal of cytidine diphosphate choline with an aqueous solution containing an organic solvent other than methanol in which a water content is 5% to 50% by volume.

20 Claims, 1 Drawing Sheet

CRYSTAL OF CYTIDINE DIPHOSPHATE CHOLINE AND PRODUCTION METHOD THEREOF

CROSS-REFERENCE TO RELATED APPLICATIONS

This patent application is the U.S. national phase of International Patent Application No. PCT/JP2017/036463, filed Oct. 6, 2017, which claims the benefit of Japanese Patent Application No. 2016-197695, filed on Oct. 6, 2016, which are incorporated by reference in their entireties herein.

TECHNICAL FIELD

The present invention relates to a crystal of cytidine diphosphate choline excellent in quality and a production method thereof.

BACKGROUND ART

Cytidine diphosphate choline is a physiologically active substance having an effect of improving brain function, and is widely used as a medicinal drug in Japan and as a health food material abroad (Patent Document 1). As a crystal of cytidine diphosphate choline, a monohydrate crystal is known (Patent Document 3), and as a production method thereof, a method in which an organic solvent is added to an aqueous solution in which cytidine diphosphate choline is dissolved is disclosed (Patent Documents 2 and 3).

When the organic solvent such as ethanol is added to the aqueous solution in which the cytidine diphosphate choline is dissolved, an organic layer and an aqueous layer are separated at normal temperature, and a long time is required for crystallization. Therefore, in order to stably obtain the crystal of cytidine diphosphate choline, a high temperature of 50° C. to 70° C. is necessary as shown in Patent Document 3.

On the other hand, if methanol having high miscibility with the aqueous solution in which the cytidine diphosphate choline is dissolved is used, a monohydrate crystal can be formed quickly even under low-temperature conditions (Patent Document 2 and Comparative Example 1 described later).

According to Non-Patent Document 1, methanol is specified in class 2 as a solvent to be regulated for a residual amount in the drug, and residue in the food, which is outside a scope of prescription management of a doctor, is undesirable. Therefore, as a material used in drugs and foods, it is strongly required to reduce residual methanol in the crystal of cytidine diphosphate choline, and in addition, it is required to have good powder properties for molding into tablets or the like.

RELATED ART

Patent Document

Patent Document 1: Japanese Patent No. 6166786
Patent Document 2: JP-B-51-32630
Patent Document 3: Japanese Patent No. 647367
Patent Document 4: Japanese Patent No. 3369236
Patent Document 5: Japanese Patent No. 4977608

Non-Patent Document

Non-Patent Document 1: Regarding guidelines of residual solvent in drugs

DISCLOSURE OF INVENTION

Problems to be Solved by the Invention

However, in a case where ethanol is used in a crystallization step, as described in Patent Document 3, when the crystal of cytidine diphosphate choline is obtained from the aqueous solution in which the cytidine diphosphate choline is dissolved at a high temperature of 50° C. to 70° C., the cytidine diphosphate choline easily decomposes, and impurities generated by the decomposition remain in a product at a high concentration (Patent Document 3 and Comparative Example 3 in Table 3 described later).

In contrast, when crystallization temperature is reduced even crystallization is allowed to take a long time, the decomposition of the cytidine diphosphate choline can be suppressed, but a specific volume of the crystal obtained this time remarkably increases and the powder properties deteriorate, then (Comparative Example 4 in Table 2 described later).

In the method described in Patent Document 2, methanol used in the crystallization step remains in the crystal at a high concentration even methanol is not used in a washing step when the crystal is filtrated (Comparative Examples 1 and 2 in Table 4 described later).

Currently, methanol certainly remains in the crystal of cytidine diphosphate choline distributed in the market (products of company A to company C in Table 4 described later). The crystal of cytidine diphosphate choline which contains no methanol and has excellent powder properties is not known until now.

Accordingly, an object of the present invention is to provide a crystal of cytidine diphosphate choline which contains no methanol and has improved powder properties, and a production method thereof.

Means for Solving the Problems

The present invention relates to the following (1) to (11).
(1) A crystal of cytidine diphosphate choline, containing no methanol and having a loose specific volume of 4.1 mL/g or less.
(2) The crystal described in above (1), wherein an angle of repose is 57 degrees or less.
(3) The crystal described in above (1) or (2), wherein an angle of rupture is 50 degrees or less.
(4) The crystal described in any one of above (1) to (3), wherein a dense specific volume is 2.1 mL/g or less.
(5) The crystal described in any one of above (1) to (4), not containing an organic solvent other than at least one organic solvent selected from the group consisting of ethanol, acetone, 1-propanol, 2-propanol, ethyl acetate, 1-butanol, 2-butanol, heptane, isopropyl acetate, methyl ethyl ketone, propyl acetate, and tetrahydrofuran.
(6) The crystal described in any one of above (1) to (5), not containing an organic solvent other than at least one organic solvent selected from the group consisting of ethanol, acetone, 1-propanol, and 2-propanol.
(7) The crystal described in any one of above (1) to (6), not containing an organic solvent other than ethanol.

(8) A method for producing a crystal of cytidine diphosphate choline, comprising: precipitating the crystal of cytidine diphosphate choline in an aqueous solution in which cytidine diphosphate choline is dissolved; collecting the precipitated crystal of cytidine diphosphate choline; and washing the collected crystal of cytidine diphosphate choline with an aqueous solution containing an organic solvent other than methanol in which a water content is 5% to 50% by volume.

(9) The production method described in above (8), wherein the organic solvent other than methanol is at least one organic solvent selected from the group consisting of ethanol, acetone, 1-propanol, 2-propanol, ethyl acetate, 1-butanol, 2-butanol, heptane, isopropyl acetate, methyl ethyl ketone, propyl acetate, and tetrahydrofuran.

(10) The production method described in (8) or (9), wherein the organic solvent other than methanol is at least one organic solvent selected from the group consisting of ethanol, acetone, 1-propanol, and 2-propanol.

(11) The production method described in any one of above (8) to (10), wherein the organic solvent other than methanol is ethanol.

Effects of the Invention

The present invention provides the crystal of cytidine diphosphate choline which contains no methanol and has improved powder properties, and the production method thereof.

EMBODIMENTS FOR CARRYING OUT THE INVENTION

1. Crystal of the Present Invention

Figure 1:
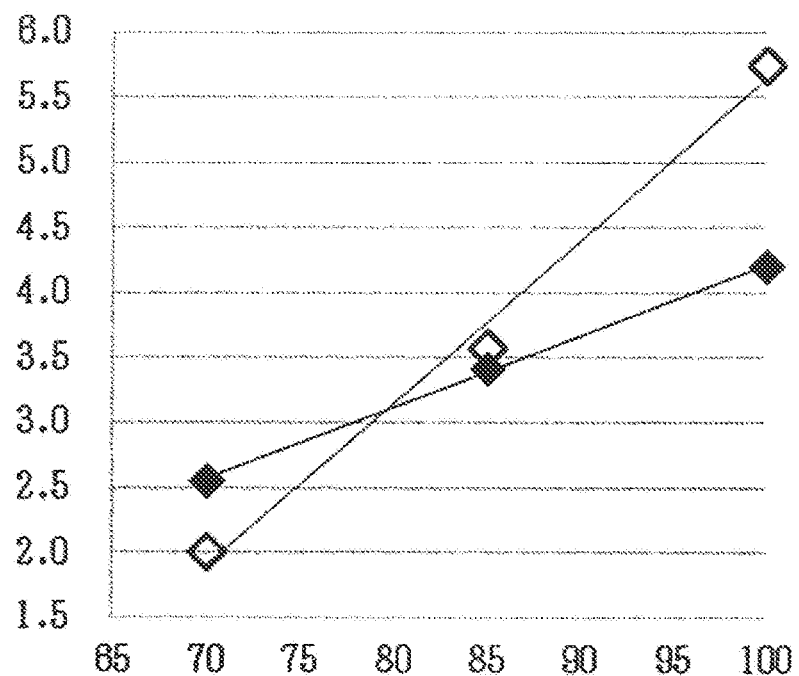
FIG. 1 describes a correlation between a loose specific volume and an ethanol concentration of an ethanol aqueous solution used for crystal washing in a crystal of cytidine diphosphate choline obtained in Comparative Examples 3 and 4 and Examples 1 to 4. A vertical axis represents the loose specific volume (mL/g), and a horizontal axis represents the ethanol concentration (% by volume). A black rhombus represents a result of crystallization at 70° C., and a white rhombus represents a result of crystallization at 30° C.

The crystal of the present invention is a crystal of cytidine diphosphate choline containing no methanol and having a loose specific volume of 4.1 mL/g or less.

Examples of an embodiment of the crystal of the present invention can include the crystal of cytidine diphosphate choline containing no methanol and having a loose specific volume of preferably 3.6 mL/g or less, more preferably 3.1 mL/g or less, and most preferably 2.6 mL/g or less.

A crystal having a small loose specific volume has excellent filling properties and is easy to handle in various processing steps, and also its transport cost is low. Therefore, the crystal of cytidine diphosphate choline preferably has a small loose specific volume, but examples of a lower limit of the loose specific volume can include generally 1.0 mL/g or more, and preferably 1.2 mL/g or more.

Here, the "loose specific volume" refers to a value which is obtained by dividing a volume occupied by a powder by a mass when the powder is filled in a container and the mass of the powder is measured.

The loose specific volume can be measured using Multi Tester MT-1001T (manufactured by Seishin Enterprise Co., Ltd.) according to the accompanying manual under the following conditions based on the 17th revision, Pharmacopoeia of Japan.

[Measurement Conditions for Loose Specific Volume]

Apparatus for use: multi-tester MT-1001T type (manufactured by Seishin Enterprise Co., Ltd.)

Sieve: 1.18 mm

Vibration range: 0.7 mm to 0.8 mm

Crystal capacity: 100 mL

Specific example of method of measuring loose specific volume: A 100 mL cylindrical container made of stainless steel is filled while the crystal is dropped via a 1.18 mm sieve vibrated at a range of 0.7 mm to 0.8 mm. Excess powder is carefully rubbed off from the top surface of the container, and the mass of the powder is measured by subtracting the mass of an empty measurement container measured in advance. The measurement is independently performed three times to determine an average value.

That the crystal of the present invention does not contain methanol can be confirmed according to a method described in the following analysis example using a gas chromatograph.

That the crystals of the present invention does not contain methanol means that methanol is below a detection limit when analyzed according to the following analysis example using the gas chromatograph.

Analysis Example Using Gas Chromatograph

Apparatus for use: GC-2014 (manufactured by Shimadzu Corporation)

Column filler: Adsorb P-1 60/80 mesh (manufactured by Nishio Kogyo Co., Ltd.)

Column temperature: 120° C.

Vaporization chamber temperature: 150° C.

Helium flow rate: 30 mL/min

Detector temperature: 200° C.

Sample preparation method: About 1.0 g of the crystal of cytidine diphosphate choline is weighed, dissolved in distilled water, and adjusted to 10 mL to obtain a sample.

Examples of an embodiment of the crystal of the present invention can include the crystal of cytidine diphosphate choline containing no methanol, having a loose specific volume of 4.1 mL/g or less, and having an angle of repose of preferably 57 degrees or less, more preferably 55 degrees or less, still more preferably 53 degrees or less, and most preferably 50 degrees or less.

The crystal having a large angle of repose cannot be completely discharged from the bottom of a hopper unless the angle of tilt of the bottom of the hopper is larger than the angle of repose when discharging the crystal from the hopper, and therefore, the device is limited and handling becomes complicated. Further, the crystal having a large angle of repose has poor flowability. Therefore, the crystal of cytidine diphosphate choline preferably has a small angle of repose, but examples of a lower limit of the angle of repose can include generally 30 degrees or more, and preferably 35 degrees or more.

Here, the "angle of repose" refers to an angle formed by a horizontal plane and a generating line of a cone formed with a powder when the powder is allowed to gently fall onto the horizontal plane through a kind of a funnel.

The angle of repose can be measured using Multi Tester MT-1001T (manufactured by Seishin Enterprise Co., Ltd.) according to the accompanying manual under the following conditions.

[Measurement Conditions for Angle of Repose]
Apparatus for use: multi-tester MT-1001T type (manufactured by Seishin Enterprise Co., Ltd.)
Sieve: 1.18 mm
Vibration range: 0.7 mm to 0.8 mm Specific example of method of measuring angle of repose: The crystal is piled on an repose angle table (component number: MT-1028) while dropped via a 1.18 mm sieve vibrated at a range of 0.7 mm to 0.8 mm. The repose angle table is rotated without giving vibration, angles are read at three sites, and an arithmetic mean thereof is determined to be the angle of repose.

Examples of an embodiment of the crystal of the present invention can include the crystal of cytidine diphosphate choline containing no methanol, having a loose specific volume of 4.1 mL/g or less, and having an angle of rupture of preferably 50 degrees or less, more preferably 48 degrees or less, still more preferably 46 degrees or less, and most preferably 44 degrees or less. Examples of a lower limit of the angle of rupture can include generally 30 degrees or more, and preferably 35 degrees or more.

Here, the "angle of rupture" refers to an angle formed by a horizontal plane and a generating line of a cone which is formed when a certain impact is applied indirectly to a cone formed with a powder when the powder is allowed to gently fall onto the horizontal plane through a kind of a funnel.

The angle of rupture can be measured using Multi Tester MT-1001T (manufactured by Seishin Enterprise Co., Ltd.) according to the accompanying manual by the following method.

Specific Example of Method of Measuring Angle of Rupture

A weight attached to the bottom of a repose angle table unit (component number: MT-1028) is slowly lifted under a tapping table and allowed to fall after the measurement of the angle of repose. This operation is repeated three times. In the same manner as the method of measuring the angle of repose, angles are read at three sites, and the arithmetic mean thereof is determined to be the angle of rupture.

Examples of an embodiment of the crystal of the present invention can include the crystal of cytidine diphosphate choline containing no methanol, having a loose specific volume of 4.1 mL/g or less, and having a dense specific volume of preferably 2.1 mg/L or less, more preferably 2.0 mg/L or less, still more preferably 1.9 mg/L or less, and most preferably 1.7 mg/L or less.

A crystal having a small dense specific volume has an excellent filling property, and also its transport cost is low. Therefore, the crystal of cytidine diphosphate choline preferably has a small dense specific volume, but examples of a lower limit of the dense specific volume can include generally 0.8 mL/g or more, and preferably 1.0 mL/g or more.

Here, the "dense specific volume" refers to a value which is obtained by dividing a volume occupied by a powder by a mass when the powder is filled in a container, a certain impact is applied to the container, and then the mass of the powder is measured.

The dense specific volume can be measured, for example, using Multi Tester MT-1001T (manufactured by Seishin Enterprise Co., Ltd.) according to the accompanying manual under the following conditions based on the 17th revision, Pharmacopoeia of Japan.

[Measurement Conditions for Dense Specific Volume]
Apparatus for use: multi-tester MT-1001T type (manufactured by Seishin Enterprise Co., Ltd.)
Sieve: 1.18 mm
Vibration range: 0.7 mm to 0.8 mm
Crystal capacity: 100 mL
Spacer: 32 mm
Tapping rate: 1 tap/sec
Number of taps: 400 taps Specific example of method of measuring dense specific volume: A 100 mL cylindrical container made of stainless steel equipped with an auxiliary cylinder is filled while the crystal is dropped via a 1.18 mm sieve vibrated at a range of 0.7 mm to 0.8 mm. The auxiliary cylinder is removed after repeating the tapping of 1 tap/sec 400 times interposing the spacer of 32 mm, and excess powder is carefully rubbed off from the top surface of the container, and the mass of the powder is measured by subtracting the mass of an empty measurement container measured in advance. The measurement is independently performed three times to determine an average value.

Examples of an embodiment of the crystal of the present invention can include the crystal of cytidine diphosphate choline containing no methanol, having a loose specific volume of 4.1 mL/g or less, and having a difference between the angle of repose and the angle of rupture of preferably 9.0 or less, more preferably 8.5 or less, still more preferably 7.0 or less, further more preferably 5.0 or less, and most preferably 4.0 or less.

A crystal having a large difference between the angle of repose and the angle of rupture has high floodability and is difficult to control, and therefore, the difference between the angle of repose and the angle of rupture is preferably small.

Examples of an embodiment of the crystal of the present invention can include the crystal of cytidine diphosphate choline containing no methanol, having a loose specific volume of 4.1 mL/g or less, and preferably not containing an organic solvent other than at least one organic solvent selected from the group consisting of ethanol, acetone, 1-propanol, 2-propanol, ethyl acetate, 1-butanol, 2-butanol, heptane, isopropyl acetate, methyl ethyl ketone, propyl acetate, and tetrahydrofuran, more preferably not containing an organic solvent other than at least one organic solvent selected from the group consisting of ethanol, acetone, 1-propanol, and 2-propanol, and most preferably not containing an organic solvent other than ethanol.

Examples of an embodiment of the crystal of the present invention can include the crystal of cytidine diphosphate choline containing no methanol, having a loose specific volume of 4.1 mL/g or less, and having a content of the above organic solvent of preferably 1000 mass ppm or less, more preferably 800 mass ppm or less, still more preferably 600 mass ppm or less, and most preferably 500 mass ppm or less.

The content of the organic solvent in the crystal of the present invention can be measured by, for example, analysis using the gas chromatograph.

Examples of an embodiment of the crystal of the present invention can include the crystal of cytidine diphosphate choline containing no methanol, having a loose specific volume of 4.1 mL/g or less, and having a peak area of 5' cytidylic acid of preferably 0.27 or less, more preferably 0.20 or less, still more preferably 0.15 or less, and most preferably 0.10 or less with respect to a peak area 100 of the cytidine diphosphate choline in high performance liquid chromatography (hereinafter referred to as HPLC) analysis.

The 5' cytidylic acid is a compound generated by decomposition of the cytidine diphosphate choline depending on heating or change of pH.

The HPLC analysis means that a compound to be analyzed is dissolved in a solvent and subjected to analysis by HPLC.

Examples of the HPLC analysis can include an analysis method capable of simultaneously detecting cytidine diphosphate choline, 5' cytidylic acid, and uridine diphosphate choline in which analysis conditions are not particularly limited, and preferably an HPLC analysis method of detecting and measuring absorbance at 254 nm.

Examples of the HPLC analysis method can include an HPLC analysis example described below.

HPLC Analysis Example

Apparatuses for use: detector (L-7405), pump (L-7100), autosampler (L-7200), column oven (L-2350) (all manufactured by Hitachi, Ltd.), chromatograph pack (C-R8A), data analysis (PAC solution) (all manufactured by Shimadzu Corporation)

Detector: ultraviolet absorptiometer (measurement wavelength: 254 nm)

Column: Partisil 10SAX, particle size: 10 μm, two columns of 4.0×250 mm are connected in series (Hichrom)

Mobile phase: 0.06 mol/L of a potassium dihydrogen phosphate aqueous solution adjusted to pH 3.5 with phosphoric acid (40.83 g of potassium dihydrogen phosphate is dissolved in distilled water, adjusted to pH 3.5 by adding phosphoric acid, and then adjusted to 5000 mL with distilled water)

Column temperature: 30° C.

Flow rate: 0.4 mL/min to 0.5 mL/min (adjusted so that retention time of the cytidine diphosphate choline is about 26 min)

Sample injection volume: 20 μL

Sample preparation method: About 0.1 g of the crystal of cytidine diphosphate choline is weighed, dissolved in distilled water, and adjusted to 100 mL to obtain a sample.

In the present specification, the peak area in the HPLC analysis is a value when measured under HPLC analysis conditions described in the HPLC analysis example. However, analysis conditions equivalent to the analysis conditions are also included in the HPLC analysis conditions in the present specification.

The peak area refers to an area of a part surrounded by a baseline and a peak line when the HPLC analysis is performed, and the peak area for each compound detected by the HPLC analysis can be determined.

Examples of an embodiment of the crystal of the present invention can include the crystal of cytidine diphosphate choline containing no methanol, having a loose specific volume of 4.1 mL/g or less, and having a peak area of uridine diphosphate choline of preferably 0.56 or less, more preferably 0.30 or less, still more preferably 0.10 or less, and most preferably 0.06 or less with respect to a peak area 100 of the cytidine diphosphate choline in the HPLC analysis.

The uridine diphosphate choline is a compound generated by decomposition of the cytidine diphosphate choline depending on heating or change of pH.

2. Production Method of Crystal of the Present Invention

A method for producing a crystal of the present invention is a method for producing the crystal of cytidine diphosphate choline comprising precipitating the crystal of cytidine diphosphate choline in an aqueous solution in which the cytidine diphosphate choline is dissolved, collecting the precipitated crystal of cytidine diphosphate choline, and washing the collected crystal of cytidine diphosphate choline with an aqueous solution containing an organic solvent other than methanol in which a water content is 5% to 50% by volume.

Hereinafter, each step will be described.

(Step of Precipitating Crystal of Cytidine Diphosphate Choline in Aqueous Solution in which Cytidine Diphosphate Choline is Dissolved)

The cytidine diphosphate choline contained in the aqueous solution in which the cytidine diphosphate choline is dissolved may be produced by a production method of any of a fermentation method, an enzyme method, an extraction method from natural substances, a chemical synthesis method, and the like.

Examples of a method of obtaining the aqueous solution in which the cytidine diphosphate choline is dissolved can include a method of dissolving the obtained cytidine diphosphate choline in water, a method of removing insoluble substances from a culture containing the cytidine diphosphate choline obtained by culturing a microorganism capable of producing the cytidine diphosphate choline [Japanese Patent No. 3369236 (Patent Document 4)] and the like, and a method described in Japanese Patent No. 4977608 (Patent Document 5).

In a case where the aqueous solution in which the cytidine diphosphate choline is dissolved contains a solid substance which is an obstacle of crystallization, the solid substance can be removed using centrifugation, filtration, a ceramic filter, or the like.

In addition, in a case where the aqueous solution in which the cytidine diphosphate choline is dissolved contains water-soluble impurities or salts which are an obstacle of crystallization, it is possible to remove the water-soluble impurities or salts by passing through a column filled with an ion exchange resin or the like.

In addition, in a case where the aqueous solution in which the cytidine diphosphate choline is dissolved contains hydrophobic impurities which are an obstacle of crystallization, it is possible to remove the hydrophobic impurities by passing through a column filled with an synthetic adsorption resin, activated carbon, or the like.

A concentration of the cytidine diphosphate choline in the aqueous solution in which the cytidine diphosphate choline is dissolved can be adjusted to preferably 200 g/L or more, more preferably 250 g/L or more, and still more preferably 300 g/L or more.

In order to set the concentration of the cytidine diphosphate choline in the aqueous solution in which the cytidine diphosphate choline is dissolved to the above concentration, the aqueous solution can be concentrated by a general concentration method such as a heating concentration method or a vacuum concentration method.

Examples of the method of precipitating the crystal of cytidine diphosphate choline in the aqueous solution in which the cytidine diphosphate choline is dissolved can include a method of cooling the aqueous solution, a method of vacuum concentrating the aqueous solution, a method of adding or dropping an organic solvent other than methanol or an aqueous solution containing the organic solvent into the aqueous solution, or a method of combining one or more thereof. The method of adding or dropping an organic solvent other than methanol or an aqueous solution containing the organic solvent into the aqueous solution is preferable, and a method of combining the method of adding or dropping an organic solvent other than methanol or an aqueous solution containing the organic solvent into the aqueous solution and the method of cooling the aqueous solution is more preferable.

In the method of cooling the aqueous solution in which the cytidine diphosphate choline is dissolved, examples of a temperature of the aqueous solution can include preferably 0° C. to 35° C., more preferably 0° C. to 30° C., and most preferably 0° C. to 25° C.

In the method of cooling the aqueous solution in which the cytidine diphosphate choline is dissolved, examples of cooling time can include preferably 2 to 100 hours, more preferably 2 to 70 hours, and most preferably 2 to 50 hours.

In the method of vacuum concentrating the aqueous solution in which the cytidine diphosphate choline is dissolved, examples of the temperature of the aqueous solution can include preferably 0° C. to 50° C., more preferably 5° C. to 45° C., and most preferably 10° C. to 40° C.

In the method of vacuum concentrating the aqueous solution in which the cytidine diphosphate choline is dissolved, examples of decompression time can include preferably 2 to 100 hours, more preferably 3 to 70 hours, and most preferably 5 to 50 hours.

In the method of adding or dropping an organic solvent other than methanol or an aqueous solution containing the organic solvent into the aqueous solution in which the cytidine diphosphate choline is dissolved, examples of the organic solvent other than methanol can include at least one organic solvent selected from the group consisting of ethanol, acetone, 1-propanol, 2-propanol, ethyl acetate, 1-butanol, 2-butanol, heptane, isopropyl acetate, methyl ethyl ketone, propyl acetate, and tetrahydrofuran, more preferably at least one organic solvent selected from the group consisting of ethanol, acetone, 1-propanol, and 2-propanol, and most preferably ethanol. In addition, a plurality of kinds of these organic solvents can also be used in combination.

Examples of a concentration of the organic solvent other than methanol contained in the aqueous solution that is added or dropped into the aqueous solution in which the cytidine diphosphate choline is dissolved can include preferably 30% by volume or more, more preferably 40% by volume or more, still more preferably 50% by volume or more, and most preferably 60% by volume or more.

Examples of the temperature of the aqueous solution when the organic solvent other than methanol or the aqueous solution containing the organic solvent is added or dropped can include preferably 0° C. to 70° C., more preferably 0° C. to 50° C., still more preferably 5° C. to 45° C., and most preferably 10° C. to 35° C.

Examples of time required for the addition or dropping of the organic solvent other than methanol or the aqueous solution containing the organic solvent can include preferably 1 to 10 hours, and more preferably 2 to 8 hours.

Examples of an amount of the aqueous solution other than methanol or the aqueous solution containing the organic solvent that is added or dropped can include preferably 1 to 10 times equivalent, more preferably of 2 to 7 times equivalent with respect to the aqueous solution in which the cytidine diphosphate choline is dissolved.

In the method of precipitating the crystal of cytidine diphosphate choline by adding or dropping the organic solvent other than methanol or the aqueous solution containing the organic solvent into the aqueous solution in which the cytidine diphosphate choline is dissolved, the organic solvent other than methanol or the aqueous solution containing the organic solvent is added or dropped, and then seed crystal may be added before the crystal of cytidine diphosphate choline precipitates.

As a seed crystal, for example, the crystal of cytidine diphosphate choline obtained by the method described in Japanese Patent No. 647367 (Patent Document 3) can be used.

Examples of time for adding the seed crystal can include preferably within 0 to 12 hours, more preferably within 0 to 8 hours, and most preferably within 0 to 4 hours after the dropping or addition of the organic solvent other than methanol or the aqueous solution containing the organic solvent is started.

The seed crystal can be added so that the concentration of the seed crystal in the aqueous solution is preferably from 0.1 g/L to 5.0 g/L, and more preferably 0.2 g/L to 1.0 g/L.

The aqueous solution containing the crystal can be matured by stirring or leaving at preferably 0° C. to 70° C., more preferably 3° C. to 50° C., and most preferably 5° C. to 35° C. for preferably 0.5 to 48 hours, more preferably 0.5 to 24 hours, and most preferably 0.5 to 12 hours after the crystal of cytidine diphosphate choline is precipitated as described above.

Maturing the crystal means that the addition of the organic solvent other than methanol or the aqueous solution containing the organic solvent is interrupted or stopped to grow the crystal.

Growing the crystal means that the crystal is increased from the precipitated crystal.

The maturing of the crystal is performed mainly for growing the crystal, but precipitation of a new crystal may occur simultaneously with the growth of the crystal.

After the crystal is matured, the step of precipitating the crystal of cytidine diphosphate choline may be resumed.
(Step of Collecting Precipitated Crystal of Cytidine Diphosphate Choline)

Examples of a method of collecting the precipitated crystal of cytidine diphosphate choline can include filtration, pressure filtration, suction filtration, and centrifugation.
(Step of Washing Collected Crystal of Cytidine Diphosphate Choline with Aqueous Solution Containing Organic Solvent Other than Methanol in which Water Content is 5% to 50% by Volume)

In one embodiment of the production method of the present invention, the collected crystal of cytidine diphosphate choline is washed with the aqueous solution containing the organic solvent other than methanol in which the water content is 5% to 50% by volume, preferably 10% to 40% by volume, and more preferably 20% to 30% by volume. By this step, adhesion of mother liquid to the crystal is reduced, and the powder properties of the crystal can be controlled in addition to improving quality of the crystal.

A temperature of the aqueous solution containing the organic solvent other than methanol used for crystal washing may be any temperature as long as the cytidine diphosphate choline does not decompose, and examples thereof can include preferably 40° C. or lower, more preferably 30° C. or lower, still more preferably 20° C. or lower, and most preferably 15° C. or lower. Examples of a lower limit of the temperature can include generally 0° C. or higher, and preferably 5° C. or higher.

As the organic solvent other than methanol used in the step of washing the crystal of cytidine diphosphate choline, one can use an organic solvent same as the organic solvent other than methanol in the method of adding or dropping the organic solvent other than methanol or the aqueous solution containing the organic solvent into the aqueous solution in which the cytidine diphosphate choline is dissolved.

Examples of the method of washing the crystal can include a method of jetting or spraying a crystal washing solution made of the aqueous solution containing the organic solvent other than methanol, and a method of immersing a crystal layer in the crystal washing solution.

In the method of immersing the crystal layer in the crystal washing solution, the crystal layer can be taken out from the crystal washing solution in which the crystal layer is immersed, suspended in the crystal washing solution again and stirred, and subjected to operations such as filtration, pressure filtration, suction filtration, and centrifugation again.

Examples of an amount of the crystal washing solution used for crystal washing can include preferably 0.5 to 10 times, more preferably 1 to 9 times, and still more preferably 2 to 8 times of volume to a weight of the crystal of cytidine diphosphate choline.

The crystal of the present invention can be obtained by drying a wet crystal obtained in this manner. The drying conditions may be any conditions as long as it is a method capable of maintaining the form of the crystal of cytidine diphosphate choline, and for example, reduced pressure drying, vacuum drying, fluidized bed drying, ventilation drying, and the like can be applied.

The drying temperature may be any temperature as long as it is in a range where adhesive water or a solvent can be removed, but examples thereof can include preferably 80° C. or lower, more preferably 70° C. or lower, and most preferably 60° C. or lower. The drying time may be any time as long as it is in a range where adhesive water or a solvent can be removed, but examples thereof can include preferably 1 to 48 hours, and more preferably 1 to 24 hours.

Comparative Example 1

In accordance with Example 1 of JP-B-51-32630 (Patent Document 2), 760 g of cytidine diphosphate choline (manufactured by Kyowa Hakko Bio Co., Ltd.: Lot. 160325) was dissolved in distilled water to 1600 mL, and an aqueous solution containing the cytidine diphosphate choline at a concentration of 450 g/L was prepared. 1600 mL of methanol was added to 400 mL of the aqueous solution at 20° C. over 20 minutes. When white turbidity was observed during the addition of methanol, 0.8 g of cytidine diphosphate choline was added as a seed crystal.

After confirming that a crystal of cytidine diphosphate choline was formed, 800 mL of ethyl acetate was added over 3 hours, followed by stirring at 20° C. for 2 hours. From about 2500 mL of crystal slurry thus obtained, 2000 mL was centrifuged, and the crystal was filtered off and washed with 640 mL of methanol. The obtained wet crystal was dried under reduced pressure at 25° C. for 3 hours, and further dried under reduced pressure at 60° C. for 3 hours to obtain 100.9 g of the crystal.

Comparative Example 2

The remainder of the crystal slurry obtained in Comparative Example 1 was centrifuged and the crystal was filtered off, and the obtained wet crystal was suspended in 160 mL of 99.5% by volume of ethanol and stirred to completely wash away methanol adhering to the crystal surface. The wet crystal was dried under reduced pressure at 25° C. for 3 hours and further dried under reduced pressure at 60° C. for 3 hours to obtain 13.2 g of the crystal.

Comparative Example 3

In accordance with Example 3 of Japanese Patent No. 647367 (Patent Document 3), 639.9 g of cytidine diphosphate choline (manufactured by Kyowa Hakko Bio Co., Ltd.: Lot. 160325) in terms of dry substances was added to 1300 mL of distilled water and dissolved to form 1690 mL of an aqueous solution. To 832 mL of the aqueous solution 640 mL of 99.5% by volume of ethanol was mixed at 70° C. Subsequently, the mixed solution was kept at 70° C. and 1280 mL of 80% by volume of hydrous ethanol was added for 2 hours.

After that, 1.28 g of the cytidine diphosphate choline was added as the seed crystal, and after stirring was continued for 30 minutes, 1280 mL of 99.5% by volume of ethanol was added over 1 hour. After that, stirring was continued for 10 hours while the solution was gradually cooled from 70° C. to 25° C. The crystal slurry thus obtained was divided into three equal parts, one of them was centrifuged and the crystal was filtered off, and then the crystal was washed with 533 mL of 99.5% by volume of ethanol. The obtained wet crystal was dried under reduced pressure at 30° C. for 3 hours, and further dried under reduced pressure at 60° C. for 3 hours to obtain 65.8 g of the crystal.

Comparative Example 4

1040 mL of an aqueous solution of cytidine diphosphate choline prepared by the same method as in Comparative Example 3 was kept at 30° C., and 800 mL of 99.5% by volume of ethanol was mixed. To the mixed solution, 1600 mL of 99.5% by volume of ethanol was added at 30° C. for 2 hours. After that, 1.6 g of the cytidine diphosphate choline was added as the seed crystal, and after confirming that the crystal was formed, 1600 mL of 99.5% by volume of ethanol was added over 2 hours.

After that, the solution was kept at 30° C. and stirring was continued for 3 hours, and then the solution was cooled to 20° C. over 3 hours. The crystal slurry thus obtained was divided into three equal parts, one of them was centrifuged and the crystal was filtered off, and then the crystal was washed with 670 mL of 99.5% by volume of ethanol. The obtained wet crystal was dried under reduced pressure at 30° C. for 3 hours, and further dried under reduced pressure at 60° C. for 3 hours to obtain 116.6 g of the crystal.

[Preliminary Test]

In to the cytidine diphosphate choline (manufactured by Kyowa Hakko Bio Co., Ltd.: Lot. 160325), 50% to 80% by volume of hydrous ethanol (water content: 20% to 50% by volume) was dissolved until remaining undissolved, and sufficiently stirred at 30° C., 35° C., or 40° C. After that, each solution was filtrated by a filter, and a concentration (g/L) of the cytidine diphosphate choline in each of obtained filtrate was measured. The results are shown in Table 1.

TABLE 1

|  | Temperature | | |
| --- | --- | --- | --- |
|  | 30° C. | 35° C. | 40° C. |
| Ethanol concentration [% by volume] 50 | 282 | 286 | 317 |
| 66 | 27.6 | 31.6 | 54.2 |
| 71 | 8.49 | 9.70 | 11.1 |
| 75 | 3.23 | 3.65 | 4.04 |
| 78 | 1.40 | 1.68 | 1.69 |
| 80 | 0.76 | 0.84 | 0.92 |

As shown in Table 1, it was found that the higher the water content in the hydrous ethanol is, the higher the solubility of the cytidine diphosphate choline is at any temperature.

EXAMPLES

Hereinafter, Examples are shown, but the present invention is not limited to the following Examples.

Example 1

One third of the crystal slurry obtained in Comparative Example 3 was centrifuged and the crystal was filtered off, and then the crystal was washed with 533 mL of 85% by volume of hydrous ethanol (water content: 15% by volume) cooled to 10° C. The obtained wet crystal was dried under reduced pressure at 30° C. for 3 hours, and further dried under reduced pressure at 60° C. for 3 hours to obtain 68.2 g of the crystal.

Example 2

One third of the crystal slurry obtained in Comparative Example 3 was centrifuged and the crystal was filtered off, and then the crystal was washed with 533 mL of 70% by volume of hydrous ethanol (water content: 30% by volume) cooled to 10° C. The obtained wet crystal was dried under reduced pressure at 30° C. for 3 hours, and further dried under reduced pressure at 60° C. for 3 hours to obtain 82.5 g of the crystal.

Example 3

One third of the crystal slurry obtained in Comparative Example 4 was centrifuged and the crystal was filtered off, and then the crystal was washed with 670 mL of 85% by volume of hydrous ethanol (water content: 15% by volume) cooled to 10° C. The obtained wet crystal was dried under reduced pressure at 30° C. for 3 hours, and further dried under reduced pressure at 60° C. for 3 hours to obtain 109.6 g of the crystal.

Example 4

One third of the crystal slurry obtained in Comparative Example 4 was centrifuged and the crystal was filtered off, and then the crystal was washed with 670 mL of 70% by volume of hydrous ethanol (water content: 30% by volume) cooled to 10° C. The obtained wet crystal was dried under reduced pressure at 30° C. for 3 hours, and further dried under reduced pressure at 60° C. for 3 hours to obtain 105.8 g of the crystal.

Figure 2:
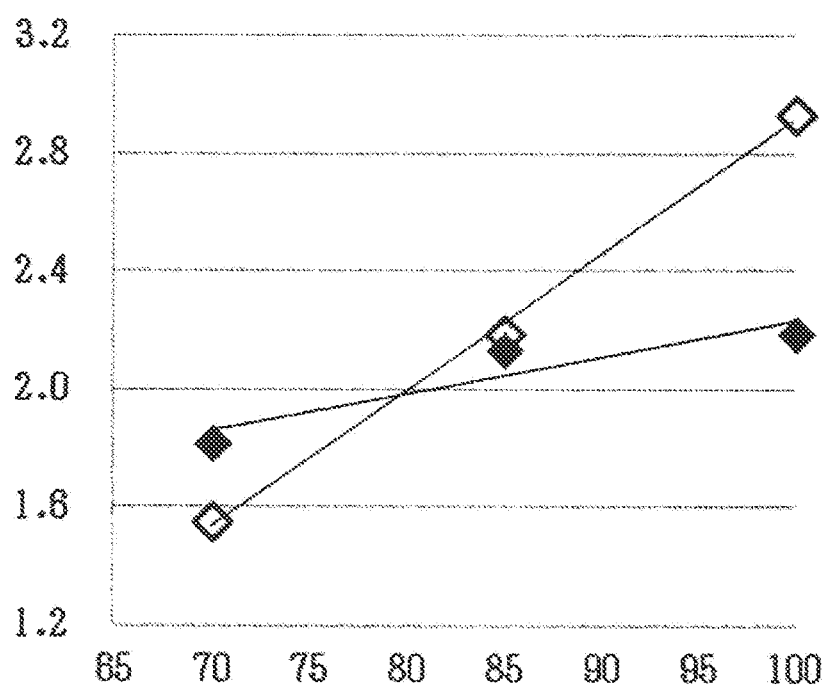
FIG. 2 describes a correlation between a dense specific volume and the ethanol concentration of the ethanol aqueous solution used for crystal washing in the crystal of cytidine diphosphate choline obtained in Comparative Examples 3 and 4 and Examples 1 to 4. A vertical axis represents the dense specific volume (mL/g), and a horizontal axis represents the ethanol concentration (% by volume). A black rhombus represents a result of crystallization at 70° C., and a white rhombus represents a result of crystallization at 30° C.

Results of measurement of the loose specific volume, the dense specific volume, the angle of repose, and the angle of rupture of the crystal of cytidine diphosphate choline circulating in the current market and the crystal of cytidine diphosphate choline obtained by the above method are shown in each of FIG. 1, FIG. 2, and Table 2.

TABLE 2

|  | Product of company A | Comparative example 1 (Patent Document 2) | Comparative example 3 (Patent Document 3) | Example 1 | Example 2 | Comparative Example 4 | Example 3 | Example 4 |
| --- | --- | --- | --- | --- | --- | --- | --- | --- |
| Crystallization |  | Methanol, Ethyl acetate | | | | Ethanol | | |
| Crystal washing |  | Methanol | | | | Ethanol | | |
| Crystallization temperature |  | 20° C. | 70° C. | | | | 30° C. | |
| Crystal washing ethanol concentration [% by volume] |  |  | 99.5 | 85 | 70 | 99.5 | 85 | 70 |
| Loose specific volume [mg/L] | 2.81 | 2.33 | 4.19 | 3.42 | 2.55 | 5.74 | 3.58 | 2.00 |
| Dense specific volume [mg/L] | 1.67 | 1.49 | 2.19 | 2.13 | 1.82 | 2.93 | 2.19 | 1.55 |
| Angle of repose [degree] | 56.6 | 49.6 | 57.4 | 46.9 | 47.2 | 48.7 | 52.8 | 43.4 |
| Angle of rupture [degree] | 48.7 | 40.1 | 50.8 | 39.6 | 38.7 | 46.4 | 47.1 | 41.6 |

FIG. 1, FIG. 2, and Table 2 show that the specific volume (loose specific volume and dense specific volume) of the crystal of cytidine diphosphate choline can be reduced at any crystallization temperature of 30° C. and 70° C. as the water content of an ethanol solution used for crystal washing is increased. In particular, in crystallization at 30° C. which is a low-temperature condition, an effect of reducing the specific volume by increasing the water content of the ethanol solution was more remarkable. Furthermore, as a result of washing the crystal of cytidine diphosphate choline using the hydrous ethanol, it was shown that the angle of repose and the angle of rupture can be reduced as compared with a case of the crystal washed by using 99.5% by volume of ethanol.

Results of measuring an amount of 5' cytidylic acid and uridine diphosphate choline contained in the crystal by HPLC analysis are shown in Table 3. Each value in Table 3 shows a value of each peak area when a peak area of the cytidine diphosphate choline is 100.

TABLE 3

|  | 5' cytidylic acid | uridine diphosphate choline |
| --- | --- | --- |
| Comparative Example 1 (Patent Document 2) | 0.085 | 0.047 |
| Comparative Example 3 (Patent Document 3) | 0.252 | 0.548 |
| Example 1 | 0.261 | 0.547 |
| Example 2 | 0.256 | 0.551 |
| Comparative Example 4 | 0.067 | 0.032 |
| Example 3 | 0.065 | 0.030 |
| Example 4 | 0.066 | 0.032 |

Table 3 shows that performing crystallization at low temperature can reduce the content of the 5'-cytidylic acid and the uridine diphosphate choline remaining in the crystal.

Subsequently, Table 4 shows results of measuring a residual solvent contained in the crystal of cytidine diphosphate choline distributed in the current market and the obtained crystal of cytidine diphosphate choline by a gas chromatograph. In Table 4, "ppm" indicates mass ppm. In addition, "N. D." indicates that it is below a detection limit.

Here, in Comparative Examples 1 and 2, about 0.5 g of the crystal of cytidine diphosphate choline was weighed, dissolved in distilled water, and adjusted to 10 mL to obtain a sample. On the other hand, in Comparative Examples 3 and 4 and Examples 1 to 4, about 1 g of the crystal of cytidine diphosphate choline was weighed, dissolved in distilled water, and adjusted to 10 mL to obtain a sample.

TABLE 4

|  | Ethanol [ppm] | Methanol [ppm] | Ethyl acetate [ppm] |
| --- | --- | --- | --- |
| Product of company A | 201 | 64 |  |
| Product of company B | 130 | 42 |  |
| Product of company C | 305 | 26 |  |
| Comparative example 1 (Patent Document 2) | N.D. | 2482 | 240 |
| Comparative Example 2 | 412 | 3937 | 667 |
| Comparative Example 3 (Patent Document 3) | 170 | N.D. | N.D. |
| Example 1 | 177 | N.D. | N.D. |
| Example 2 | 173 | N.D. | N.D. |
| Comparative Example 4 | 490 | N.D. | N.D. |
| Example 3 | 423 | N.D. | N.D. |
| Example 4 | 340 | N.D. | N.D. |

As shown in Table 4, it has been found that all crystals of cytidine diphosphate choline distributed in the current market contain methanol. From the results of Comparative Examples 1 and 2, it is found that methanol added in the crystallization step is detected at a high concentration in the crystal of cytidine diphosphate choline even when the crystal washing is performed with ethanol. From this, it has been found that the crystal of cytidine diphosphate choline has properties of easily incorporating the methanol, and the methanol added in the crystallization step and incorporated into the crystal cannot be removed by the crystal washing.

On the other hand, in Examples 1 to 4, since methanol was not used in the crystallization step and the crystal washing step, no methanol was detected in the obtained crystal of cytidine diphosphate choline.

From the above, it has been found that the crystal of cytidine diphosphate choline containing no methanol and showing powder properties equal to or higher than that of the existing crystal of cytidine diphosphate choline can be obtained by the production method of the crystal of the present invention.

While the present invention has been described in detail with reference to specific embodiments, it is apparent to those skilled in the art that various changes and modifications can be made without departing from the spirit and scope of the present invention. The present application is based on Japanese Patent Application (Japanese Patent Application No. 2016-197695) filed on Oct. 6, 2016 and the entire contents of which are incorporated herein by reference. Further, all references cited herein are incorporated herein by reference in their entirety.

INDUSTRIAL APPLICABILITY

According to the present invention, there is provided a crystal of cytidine diphosphate choline in which impurities and residual solvent are reduced and powder properties are improved at the same time, and the production method thereof.

The invention claimed is:

1. A crystal of cytidine diphosphate choline, containing no methanol and having a loose specific volume of 4.1 mL/g or less, wherein the crystal of cytidine diphosphate choline has (i) a peak area of 5' cytidylic acid of 0.20 or less and/or (ii) a peak area of uridine diphosphate choline of 0.30 or less with respect to a peak area of 100 of the cytidine diphosphate choline in a high performance liquid chromatography analysis.

2. The crystal according to claim 1, wherein an angle of repose is 57 degrees or less.

3. The crystal according to claim 1, wherein an angle of rupture is 50 degrees or less.

4. The crystal according to claim 1, wherein a dense specific volume is 2.1 mL/g or less.

5. The crystal according to claim 1, not containing an organic solvent other than at least one organic solvent selected from the group consisting of ethanol, acetone, 1-propanol, 2-propanol, ethyl acetate, 1-butanol, 2-butanol, heptane, isopropyl acetate, methyl ethyl ketone, propyl acetate, and tetrahydrofuran.

6. The crystal according to claim 1, not containing an organic solvent other than at least one organic solvent selected from the group consisting of ethanol, acetone, 1-propanol, and 2-propanol.

7. The crystal according to claim 1, not containing an organic solvent other than ethanol.

8. A method for producing the crystal of cytidine diphosphate choline of claim 1, comprising: precipitating the crystal of cytidine diphosphate choline in an aqueous solution in which cytidine diphosphate choline is dissolved; collecting the precipitated crystal of cytidine diphosphate choline; and washing the collected crystal of cytidine diphosphate choline with an aqueous solution containing an organic solvent other than methanol in which a water content is 5% to 50% by volume.

9. The production method according to claim 8, wherein the organic solvent other than methanol is at least one organic solvent selected from the group consisting of ethanol, acetone, 1-propanol, 2-propanol, ethyl acetate, 1-butanol, 2-butanol, heptane, isopropyl acetate, methyl ethyl ketone, propyl acetate, and tetrahydrofuran.

10. The production method according to claim 8, wherein the organic solvent other than methanol is at least one organic solvent selected from the group consisting of ethanol, acetone, 1-propanol, and 2-propanol.

11. The production method according to claim 10, wherein the organic solvent other than methanol is ethanol.

12. The crystal according to claim 2, wherein an angle of rupture is 50 degrees or less.

13. The crystal according to claim 12, not containing an organic solvent other than at least one organic solvent selected from the group consisting of ethanol, acetone, 1-propanol, 2-propanol, ethyl acetate, 1-butanol, 2-butanol, heptane, isopropyl acetate, methyl ethyl ketone, propyl acetate, and tetrahydrofuran.

14. The crystal according to claim 12, not containing an organic solvent other than at least one organic solvent selected from the group consisting of ethanol, acetone, 1-propanol, and 2-propanol.

15. The crystal according to claim 12, not containing an organic solvent other than ethanol.

16. The crystal according to claim 12, wherein a dense specific volume is 2.1 mL/g or less.

17. The crystal according to claim 16, not containing an organic solvent other than at least one organic solvent selected from the group consisting of ethanol, acetone, 1-propanol, 2-propanol, ethyl acetate, 1-butanol, 2-butanol, heptane, isopropyl acetate, methyl ethyl ketone, propyl acetate, and tetrahydrofuran.

18. The crystal according to claim 16, not containing an organic solvent other than at least one organic solvent selected from the group consisting of ethanol, acetone, 1-propanol, and 2-propanol.

19. The crystal according to claim 16, not containing an organic solvent other than ethanol.

20. The crystal according to claim 1, wherein the crystal of cytidine diphosphate choline has (i) a peak area of 5' cytidylic acid of 0.20 or less and (ii) a peak area of uridine diphosphate choline of 0.30 or less with respect to a peak area of 100 of the cytidine diphosphate choline in a high performance liquid chromatography analysis.

* * * * *